United States Patent
Mostert

(10) Patent No.: US 10,526,281 B2
(45) Date of Patent: Jan. 7, 2020

(54) CONTROLLING BIURET IN UREA PRODUCTION

(71) Applicant: STAMICARBON B.V., Sittard (NL)

(72) Inventor: Eelco Mostert, Heerlen (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 16/098,837

(22) PCT Filed: Apr. 28, 2017

(86) PCT No.: PCT/NL2017/050270
§ 371 (c)(1),
(2) Date: Nov. 2, 2018

(87) PCT Pub. No.: WO2017/192031
PCT Pub. Date: Nov. 9, 2017

(65) Prior Publication Data
US 2019/0194127 A1  Jun. 27, 2019

(30) Foreign Application Priority Data

May 3, 2016  (EP) ..................... 16168119

(51) Int. Cl.
*C07C 273/04* (2006.01)
*C07C 273/16* (2006.01)
(Continued)

(52) U.S. Cl.
CPC ............ *C07C 273/04* (2013.01); *B01D 53/58* (2013.01); *B01J 4/008* (2013.01); *C07C 273/16* (2013.01); *C07C 275/02* (2013.01); *C07C 275/62* (2013.01)

(58) Field of Classification Search
None
See application file for complete search history.

(56) References Cited

U.S. PATENT DOCUMENTS 3,211,788 A    10/1965  Cook
3,287,407 A *  11/1966  Zardi ..................... C05C 9/005
                                                              564/73

(Continued)

FOREIGN PATENT DOCUMENTS

| GB | 959358 | 6/1964 |
| WO | WO-2011/012324 | 2/2011 |
| WO | WO-2011/099844 | 8/2011 |

OTHER PUBLICATIONS

International Preliminary Report on Patentability for PCT/NL2017/050270, dated Aug. 2, 2018, 16 pages.

(Continued)

*Primary Examiner* — Amy C Bonaparte
(74) *Attorney, Agent, or Firm* — Morrison & Foerster LLP

(57) ABSTRACT

Disclosed is a novel method of controlling the formation of biuret in urea production, and particularly reducing, preventing or reversing such formation. This is accomplished by adding liquid ammonia to a urea aqueous stream. This addition is done at one or more positions downstream of a recovery section in a urea plant. The addition of liquid ammonia serves to shift the equilibrium of biuret formation from urea, to the side of the formation of urea from biuret and ammonia. The invention can be accomplished also in pre-existing urea plant, by the simple measure of providing an appropriate inlet for liquid ammonia, in fluid communication with a source of such liquid ammonia.

3 Claims, 1 Drawing Sheet

(51) Int. Cl.
  *C07C 275/02* (2006.01)
  *C07C 275/62* (2006.01)
  *B01D 53/58* (2006.01)
  *B01J 4/00* (2006.01)

(56) References Cited

U.S. PATENT DOCUMENTS 4,231,960 A * 11/1980 Schmidt ............... C07C 273/16
                                                          208/25
2012/0189528 A1* 7/2012 Casara .................. B01D 53/58
                                                         423/356

OTHER PUBLICATIONS

International Search Report for PCT/ NL2017/050270, dated Aug. 23, 2017, 4 pages.
Meessen, "Urea" in: Ullmann's Encyclopedia of Industrial Chemistry, Wiley-VCH Verlag GmbH & Co. KGaA, Weinheim, Germany (2010) 40 pages.

* cited by examiner

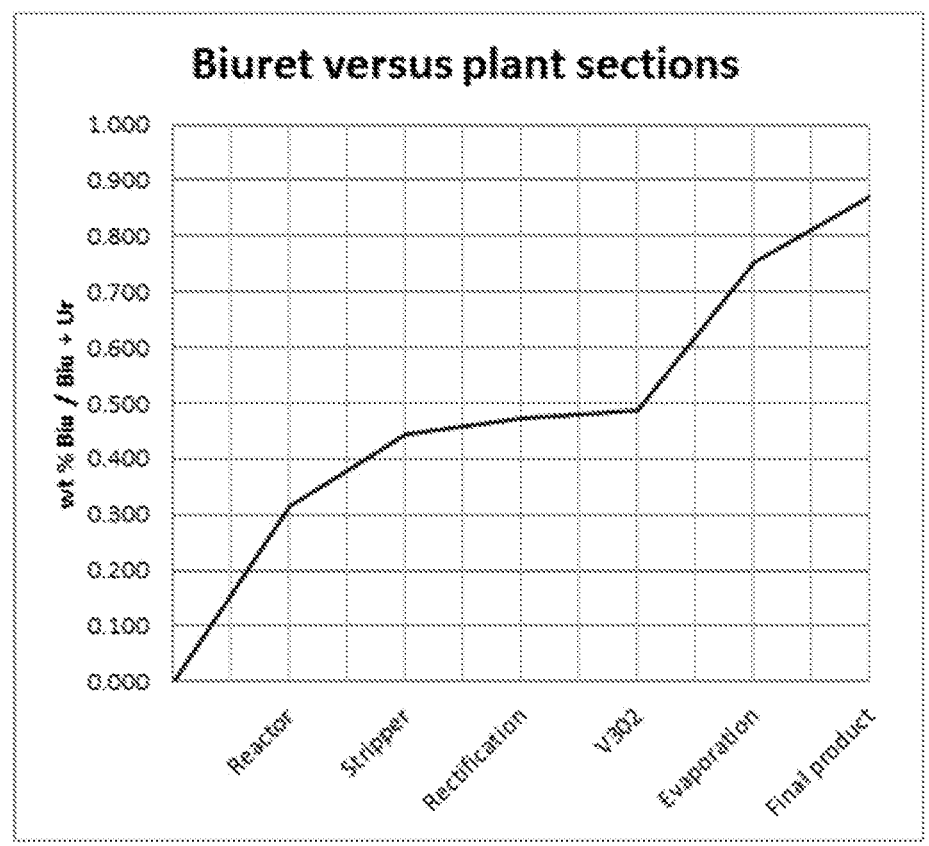

CONTROLLING BIURET IN UREA PRODUCTION

CROSS-REFERENCE TO RELATED APPLICATIONS

This application is the national phase of PCT application PCT/NL2017/050270 having an international filing date of 28 Apr. 2017, which claims benefit of European patent application No. 16168119.2 filed 3 May 2016. The contents of the above patent applications are incorporated by reference herein in their entirety.

FIELD OF THE INVENTION

The invention is in the field of urea production, and pertains to controlling the amount of biuret produced as a by-product. The invention relates to a process as well as a plant, and to modernization of pre-existing plants.

BACKGROUND OF THE INVENTION

Urea is generally produced from ammonia and carbon dioxide. It can be prepared by introducing an ammonia excess together with carbon dioxide at a pressure between 12 and 40 MPa and at a temperature between 150° C. and 250° C. into a urea synthesis zone. The resulting urea formation can be presented best in the form of two consecutive reaction steps, in the first step ammonium carbamate being formed according to the exothermic reaction:

$$2NH_3 + CO_2 \rightarrow H_2N-CO-ONH_4$$

after which the ammonium carbamate formed is dehydrated in the second step to give urea according to the endothermic equilibrium reaction:

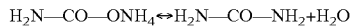

$$H_2N-CO-ONH_4 \leftrightarrow H_2N-CO-NH_2 + H_2O$$

The extent to which these reactions take place depends among other things on the temperature and the ammonia excess used. The reaction product obtained in a urea synthesis solution substantially consists of urea, water, unbound ammonia and ammonium carbamate. The ammonium carbamate and the ammonia are removed from the solution and are generally returned to the urea synthesis zone.

In addition to the above-mentioned solution in the urea synthesis zone, a gas mixture is formed which consists of unconverted ammonia and carbon dioxide together with inert gases, the so called reactor off-gas. The urea synthesis section may comprise separate zones for the formation of ammonium carbamate and urea. These zones may also be combined in a single apparatus.

Different urea production process exist. These processes, and by analogy the plants in which these processes are conducted, generally provide for the following stages: synthesis, recovery of unreacted starting materials, downstream processing, and finishing. Thereby synthesis and recovery sections are applied that are connected with each other so as to form a synthesis loop, whereby starting materials (ammonia and carbon dioxide, particularly in the form of ammonium carbamate) are recovered and recycled back to synthesis stage. The output of the synthesis loop is generally a purified aqueous urea stream, having a concentration of 50 wt. % urea or higher, generally up to 75-80 wt. % before said stream is subjected to final concentration step(s).

The downstream processing generally refers to one or more sections, zones, or units in which the aforementioned aqueous urea stream is further concentrated. Such further concentration is typically conducted by evaporation, and the concentration section is frequently referred to as an evaporation section.

The output of the concentration section is a concentrated urea aqueous stream that is often referred to as a urea melt. This melt is suitable to be converted in a urea finishing section into a solid urea product. The urea melt typically has a urea concentration of greater than 90 wt %, preferably greater than 95 wt %, such as greater than 97 wt %. From urea finishing generally a gas stream is emitted that comprises ammonia. In order to prevent ammonia emissions, modern urea production plants comprise an ammonia-abatement section (also known as an ammonia-removal section), such as an ammonia-neutralizing section. Such a neutralizing section typically comprises one or more acid scrubbers.

One of the challenges in urea production concerns controlling the amount of biuret formed as a by-product, and generally present in urea products such as prills or granules. Biuret is dimer of urea, and is formed under release of ammonia. The amount of biuret is an indicator of the urea quality as can be sold. Typically, a worldwide standard specification for biuret in urea products, is below 1 wt. %. E.g., for fertilizer purposes, the amount of biuret is generally below 0.9 wt. %. For other applications, such as the use of an aqueous urea solution in a unit for the reduction of NOx in diesel exhaust gases (particularly known as Diesel Exhaust Fluid, traded as AdBlue®), the biuret content is required to be still lower.

In urea plants operating on the basis of old, once-through technology the formation of biuret is not a significant problem. Modern plants, such as urea stripping plants, however tend to result in a higher amount of biuret formed. It remains desired to better control biuret production.

An additional problem is that it is more difficult to produce urea according to desired biuret specifications, in the event that the plant in which the urea is produced, is not operated on full capacity. Generally, biuret levels are guaranteed for a plant operating at full capacity. In practice, this means that manufacturers operating their plants at reduced capacity, run a risk that the products produced do not meet specifications for all end-uses. It would be desired to provide a urea manufacturing process, and a plant suitable for such process, that allows controlling biuret formation also in the event that the plant in which the urea is produced is operated at a reduced capacity. Further, it would be desired to provide a method of controlling biuret formation that can be implemented in an existing urea production plant without substantive, expensive modification of such a plant.

U.S. Pat. No. 3,211,788 discloses a method for the production of solid urea from anhydrous urea melt, and aims at retaining and transferring the molten urea at minimum biuret formation. According to that process an anhydrous solution of ammonia and urea is formed at the point where anhydrous urea melt is formed by evaporation of aqueous urea solution from a synthesis process. Thereto a stream of the anhydrous melt, having a temperature in the range of 135-145° C., and a pressure preferably above 200 psi, is fed to the ammoniator. An ammonia feed stream is fed to the ammoniator as well. The balance of undissolved ammonia is removed along the top of the ammoniator. Such removal along the top of the reactor can only take place provided the ammonia is in the gas phase. The ammonia-urea solution is removed along the bottom of the ammoniator and passed to solidification means, which may be physically located at a considerable distance. The fact that the urea melt is transferred to the solidification means in the form of an ammonia-urea solution permits minimizing biuret formation during such transfer.

GB959.358 discloses a process for producing urea prills which permits to reduce biuret formation. According to the process of GB959.358, urea containing degasified reactor effluent is passed from the primary purification zone to a second purification zone wherein the effluent is heated under specified conditions of temperature and pressure. Biuret formation is minimized by maintaining the urea melt in the conversion zone under an ammonia pressure of 10-100 atm., and a temperature of 272-375° F. for a period of time sufficient to achieve equilibrium between the ammonia-biuret-urea, to obtain a melt containing 0.1-0.3 wt. % biuret, which is then passed to the prilling zone. The biuret concentration is further reduced by contacting the urea melt with an ammonia containing gas at a temperature above the melting point of pure urea, for a period of time sufficient to achieve equilibrium between the reacting ammonia and biuret and urea.

SUMMARY OF THE INVENTION

In order to better address one or more of the aforementioned desires, the invention provides, in one aspect, a process for producing urea, the process comprising
 a. subjecting ammonia and carbon dioxide to urea forming conditions in a urea synthesis section, thereby producing a urea aqueous stream;
 b. sending the urea aqueous stream to a recovery section;
 c. subjecting, in the recovery section, the urea aqueous stream to recovery of unreacted ammonia and carbon dioxide from said urea aqueous stream, thereby producing recovered ammonia and carbon dioxide, and a purified urea aqueous stream;
 d. recycling said recovered ammonia and carbon dioxide to the synthesis section;
 e. sending the purified urea aqueous stream to a concentration section;
 f. subjecting, in the concentration section, the purified urea aqueous stream to removal of water, thereby producing a concentrated urea stream;
wherein the process further comprises adding, downstream of the recovery section, an ammonia-comprising liquid to the urea aqueous stream, preferably to the concentrated urea stream, and wherein the process is conducted in a urea plant provided with an abatement section (such as a neutralizing section) for ammonia-containing gas emissions.

In another aspect, the invention presents a plant for the production of urea, said plant comprising a urea synthesis section having an inlet for ammonia and carbon dioxide and an outlet for a urea aqueous solution, said outlet being in fluid communication with a recovery section having an inlet for the urea aqueous solution, an outlet for ammonia and carbon dioxide recycle, and an outlet for a purified urea aqueous stream, said outlet for ammonia and carbon dioxide recycle being in fluid communication with an inlet of the synthesis section, recovery section, said outlet for a purified urea aqueous stream being in fluid communication with an inlet of a concentration section; said concentration section having an outlet for steam or steam condensate, and an outlet for a concentrated urea stream which is in fluid communication with a finishing section for the concentrated urea stream, said finishing section comprising a gas outlet in gas flow connection with an abatement-section, such as a neutralizing section, for ammonia-containing gas emissions, wherein the plant comprises, downstream of the recovery section (such as in a concentration section or in a finishing section), a supply member for supplying liquid ammonia to an inlet for liquid ammonia.

In a still further aspect, the invention is a method of modernizing a pre-existing plant for the production of urea, said plant comprising a urea synthesis section having an inlet for ammonia and carbon dioxide and an outlet for a urea aqueous solution, said outlet being in fluid communication with a recovery section having an inlet for the urea aqueous solution, an outlet for ammonia and carbon dioxide recycle, and an outlet for a purified urea aqueous stream, said outlet for ammonia and carbon dioxide recycle being in fluid communication with an inlet of the synthesis section, said outlet for a purified urea aqueous stream being in fluid communication with an inlet of a concentration section; said concentration section having an outlet for steam or steam condensate, or another heat exchange medium, and an outlet for a concentrated urea stream, which is in fluid communication with a finishing section for the concentrated urea stream, said finishing section comprising a gas outlet in gas flow connection with an abatement section, such as a neutralizing section, for ammonia-containing gas emissions, the modernizing method comprising adding a supply member for supplying liquid ammonia to an inlet for liquid ammonia downstream of the recovery section.

DESCRIPTION OF THE DRAWING

FIG. 1 is a graph originating from the present inventors and representing the formation of biuret in the sections of a conventional urea stripping plant, when operated in a conventional manner. The sections are indicated on the X-axis, with the upstream side left and the downstream side right. The section "rectification" is in fact part of a recovery section. The section "V302" is a urea storage tank. The cumulative percentages of biuret formed are indicated on the X-axis as a percentage of biuret over the sum of urea and biuret. The graph indicates that, in addition to the conventional belief that biuret is mainly formed in the stripper, a substantial amount of the biuret is formed in the evaporation (i.e., concentration) and finishing sections.

DETAILED DESCRIPTION OF THE INVENTION

The invention is based, in a general sense, on the judicious insight to add ammonia in order to reduce biuret formation. The formation of biuret from urea, in which ammonia is formed, is a chemical equilibrium. By adding ammonia to a urea aqueous stream that is under biuret-forming conditions, the equilibrium will be shifted in favor of the reverse reaction, i.e., to the side of the starting material (viz. urea). As a result, the formation of biuret will be reduced, prevented, or even reversed. It will be understood that the extent to which biuret formation can be prevented or reversed, will depend on the amount of ammonia added, the residence time of the mixture of urea and ammonia, and the temperature. E.g., in the event that liquid ammonia is added downstream of a concentration section, such as to a concentrated urea aqueous stream (such as to a urea melt having 2-5 wt., % of water), a suitable ammonia concentration after addition is in a range of from 500 to 5000 ppm by weight. A typical temperatures thereby is in a range of from 130° C. to 140° C.

Adding ammonia to a urea process reflects a counter-intuitive measure, since a urea plant is normally designed such as to recover ammonia from the urea product, and particularly to prevent ammonia from being vented into the air. Interestingly, however, modern urea plants will comprise one or more acid-scrubbers downstream of urea finishing, which serve to neutralize ammonia before gas streams containing such ammonia are vented into the air. The inventors have realized that the presence of such scrubbers, or of any other available measures that are applied in a urea plant so as to reduce ammonia emissions, in fact make it possible to even add ammonia to the urea stream produced in the plant.

Hitherto, controlling the formation of biuret has focused on events in the urea synthesis section. This is consistent with the general belief that most of the biuret is formed in the stripper. The inventors now believe, without wishing to be bound by theory, that a substantial part of biuret is produced in the concentration and/or finishing sections.

In accordance with the invention, the above insights are put to use by controlling the formation of biuret at the process stage where a concentrated urea stream (urea melt) is formed.

The invention can be easily implemented in any urea plant. Such a plant will generally comprise at least the following sections: a urea synthesis section, a recovery section, and a concentration section. Typically, a urea production plant will also comprise a finishing section downstream of the concentration section, in which a urea melt obtained from the concentration section is converted into a final, solid product such as prills or granules. The foregoing sections are in such fluid communication as is known in the art, generally providing for a urea synthesis loop to which recovered ammonia and carbon dioxide (including ammonium carbamate) are recycled back.

The urea synthesis section comprises one or more inlets for a feed of reactants, viz. ammonia and carbon dioxide. In view of the necessary urea-forming conditions, the synthesis section will generally be operated under a high pressure (typically 12-40 MPa) and is customarily referred to as a HP (high pressure) section. The synthesis section usually comprises a reactor, and the inlets can be provided in the reactor. In many urea plants, the synthesis section also comprises other HP equipment, such as a stripper and a condenser. The stripper can be a thermal stripper (which operates on the basis of heat only), but more customarily is a stripper operating on the basis of a stripping gas (ammonia or, more commonly, carbon dioxide). The inlets for feed reactants into the synthesis section can also be comprised in such other equipment. E.g., a frequently used process is a carbon dioxide stripping processes, in which typically a carbon dioxide feed is applied as a stripping gas, and is made to enter the synthesis section via an inlet to the stripper.

The synthesis section has an outlet (i.e., a liquid outlet) for a urea aqueous solution (i.e., a urea synthesis solution resulting from subjecting ammonia and carbon dioxide to urea-forming conditions) that is in fluid communication with at least one recovery section (sometimes also referred to as a recirculation section). This generally comprises one or more sections operated at a pressure below 7 MPa. This can be a low pressure (LP) section, a medium pressure (MP) section, or both. LP generally is 0.1 to 1 MPa, MP is generally 1 to 7 MPa, more typically 1-5 MPa.

For completeness' sake, it is mentioned that the synthesis section will also comprise, e.g., at the reactor, a gas outlet for inert gases (via which some unreacted gaseous ammonia and carbon dioxide will also be emitted), which gases will generally be sent to a high pressure scrubber. Also, in the event of a stripping process as mentioned above, the stripper will have a gas outlet for unreacted gaseous ammonia and/or carbon dioxide and, if applicable, also for utilized stripping gas).

The at least one recovery section has an inlet for the aforementioned urea aqueous solution resulting from synthesis. In the recovery section, unreacted ammonia and carbon dioxide are recovered, and recycled back to the synthesis section. The recovery section therefore comprises an outlet for ammonia and carbon dioxide recycle, which is in fluid communication with an inlet of the synthesis section. The recycle frequently takes the form of a LP ammonium carbamate stream, which is brought up to synthesis pressure prior to entering the synthesis section. The recovery section comprises an outlet for a urea aqueous solution, which is purified as a result of the ammonium carbamate recovery in the recovery section. Said outlet is in fluid communication with downstream sections, thereby (directly or indirectly) with an inlet of a concentration section. The concentration section serves to increase the urea concentration by removal of water. This is generally accomplished by evaporation, and the concentration section has an outlet for water, i.e., typically either a gas outlet for steam or a liquid outlet for steam condensate. The concentration section also comprises an outlet for the concentrated urea stream that results from the removal of water in the concentration section. The concentrated urea stream is often referred to as a urea melt which is suitable to be converted in a urea finishing section in a solid urea product. The urea melt typically has a urea concentration of greater than 90 wt %, preferably greater than 95 wt %, such as greater than 97 wt %. The urea melt is sent to a finishing section where it is generally shaped into a solid form such as prills or granules.

The invention, in all its embodiments, can be realized in any type of urea plant. In practice, in view of the general requirements on ammonia emissions, the invention can only be conducted in a urea plant having an abatement section, such as a neutralization section, for ammonia-containing gas emissions. Typically, such a section is an ammonia abatement section comprising one ore more of comprises one or more of, e.g., absorbers, incinerators and scrubbers; scrubbers may be for example acidic scrubbers. In the acidic scrubbers the ammonia containing gas stream is contacted with a weak or strong acid. Examples are acetic acid, nitric acid, sulphuric acid. Absorbers can contain solid adsorbents, see, e.g., WO2011/099844.

Urea plants are known to the skilled person. Reference is made to Ullmann's Encyclopedia of Industrial Chemistry, 2010, A27, pages 333-350 on urea.

The addition of liquid ammonia in accordance with the invention takes place downstream of the recovery section or sections. At this point, a purified urea aqueous stream results, to which liquid ammonia can be added.

The liquid ammonia can be added to a urea storage tank that is typically provided upstream of a concentration section. To this end, the urea storage tank will comprise an inlet for liquid ammonia, which inlet will be in fluid communication with a source of said liquid ammonia.

The addition of liquid ammonia can also be accomplished in the concentration section. In that event one or more of the concentrators (typically: evaporators) will be provided with an inlet for liquid ammonia. This inlet is to be connected, by fluid communication, to a source of liquid ammonia.

Preferably, the liquid ammonia is added downstream of the concentration section. At this point, a concentrated urea aqueous stream results, typically having a urea concentration of more than 90 wt. % (a urea melt, as discussed hereinbefore). In this embodiment, the liquid ammonia can be added still upstream of the finishing section, or into the finishing section.

The liquid ammonia can also be added in more than one manner, i.e. in any combination of the foregoing points of addition.

In a preferred embodiment, the invention pertains to a process for the preparation of urea according to a stripping process, as conducted in a urea stripping plant.

In a urea stripping plant the decomposition of the ammonium carbamate that has not been converted into urea and the expulsion of the usual ammonia excess largely takes place at a pressure that is essentially almost equal to the pressure in the synthesis reactor. This decomposition and expulsion take place in one or more stripper(s) installed downstream of the reactor, possibly with the aid of a stripping gas such as, for example, carbon dioxide and/or ammonia, and with the addition of heat. It is also possible to apply thermal stripping. Thermal stripping means that use is made exclusively of the supply of heat to decompose ammonium carbamate and remove the ammonia and carbon dioxide present from the urea solution. The gas stream leaving a stripper contains ammonia and carbon dioxide which are condensed in a high-pressure condenser and then returned to the urea synthesis zone.

In a urea stripping plant the synthesis zone is operated at a temperature of 160-240° C. and preferably at a temperature of 170-220° C. The pressure in the synthesis reactor is 12-21 MPa, preferably 12.5-20 MPa, more preferably 13-16 MPa. In the art, these ranges are generally considered to represent "high pressure" (as also used in connection with a conventional "High Pressure Carbamate Condenser"). The gross ammonia to carbon dioxide molar ratio (gross N/C ratio) in the urea synthesis zone of a stripping plant usually is in between 2.2 and 5 and preferably between 2.5 and 4.5 mol/mol. For completeness' sake, it is noted that the synthesis zone will usually operate on the basis of both an external feed of the starting materials, ammonia and carbon dioxide, and recycled starting materials, generally comprising recycled ammonia and carbon dioxide in a free form as well as in the form of ammonium carbamate and/or biuret. The gross N/C ratio, which is a term having a customary meaning in the art, refers to a hypothetical mixture in which all starting materials are converted into free ammonia and carbon dioxide.

The synthesis zone can comprise a single reactor or a plurality of reactors, arranged in parallel or in series. In addition to one or more reactors, the synthesis section comprises a stripper, a condenser and a scrubber, all operating at substantially the same pressure. The synthesis zone is generally referred to as a High Pressure (HP) section.

In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, high pressure (HP) steam is added to heat the solution via indirect heat exchange. The urea solution leaves the heat exchanger at the bottom part, while the vapor phase leaves the stripper at the top part. The vapor leaving said stripper contains ammonia, carbon dioxide and a small amount of water. Said vapor is condensed in a falling film type heat exchanger or a submerged type of condenser that can be a horizontal type or a vertical type. A horizontal type submerged heat exchanger is described in the aforementioned Ullmann's Encyclopedia of Industrial Chemistry, Vol. A27, 1996, pp 333-350.

After the stripping treatment, the pressure of the stripped urea solution is reduced in a urea recovery section. In the recovery section the non-converted ammonia and carbon dioxide in the urea solution are separated from the urea and water solution. A recovery section comprises usually a heater, a liquid/gas separation section and a condenser. The urea solution entering a recovery section is heated to vaporize the volatile components ammonia and carbon dioxide as well as water from that solution. The heating agent used in the heater is usually steam. The ammonium carbamate aqueous solution formed in a low pressure carbamate condenser in the recovery section, operated at a lower pressure than the pressure in the synthesis section, is preferably returned to the urea synthesis section operating at synthesis pressure. The recovery section is generally a single section or can be a plurality of recovery sections arranged in parallel or in series. The recovery section comprises a heater, a liquid/gas separator and a condenser. The pressure in this recovery section is generally between 200 to 600 kPa. This section is generally referred to as a low pressure (LP) recovery section (or recirculation section, the terms "recovery section" and "recirculation section" in this description are used interchangeably). In the heater of the recovery section the bulk of ammonia and carbon dioxide is separated from the urea and water phase by heating the urea solution. Usually low pressure (LP) steam is used as heating agent. The urea and water phase contains a small amount of dissolved ammonia and carbon dioxide that leaves the recovery section and is sent to a downstream urea processing section where the urea solution is concentrated by evaporating the water from said solution. This section, i.e., the concentration section, is frequently referred to as the evaporation section and it is typically comprised of one or two evaporators, whose vapors are condensed downstream and recycled back to the process.

In some embodiments, in addition to the HP synthesis section and the LP recovery section, a medium pressure (MP) treatment section is present. E.g., WO 02/090323 discloses a urea process and plant of the carbon dioxide stripping type, wherein a MP treatment section is present parallel with the HP stripping section. A similar disclosure is found in EP 2 086 928.

Processes also exist in which a MP treatment section is present in series, downstream of the urea synthesis section. In this respect reference can be made to, e.g., GB 1 542 371, and other disclosures of the Snamprogetti Ammonia and Self-Stripping processes.

In urea stripping plants, generally more biuret is formed than in conventional once-through plants. A great benefit of the present invention is that, provided that a sufficient amount of ammonia is added and that the urea aqueous stream is allowed to have a long enough residence time with the ammonia, also amounts of biuret formed in the synthesis section (such as in the stripper) can be reduced.

An important advantage of the present invention resides in the simplicity of the measure to add liquid ammonia. The invention can be provided in a new (grassroots) plant, as well as in a pre-existing plant. In the latter case, no great changes, and no big investments, need to be made. The invention merely requires the simple measure of providing an inlet for liquid ammonia at a position downstream of the recovery section, as discussed hereinbefore. To the extent not already present, making an additional liquid inlet can be easily done (e.g. by creating a bore hole in a pipe or a vessel, and connecting same to a source of ammonia).

In sum, the invention provides a novel method of controlling the formation of biuret in urea production, and particularly reducing, preventing or reversing such formation. This is accomplished by adding liquid ammonia to a urea aqueous stream. This addition is done at one or more positions downstream of a recovery section in a urea plant. The addition of liquid ammonia serves to shift the equilibrium of biuret formation from urea, to the side of the formation of urea from biuret and ammonia. The invention can be accomplished also in pre-existing urea plant, by the simple measure of providing an appropriate inlet for liquid ammonia, in fluid communication with a source of such liquid ammonia.

Where in this description, the component parts of a urea plant are discussed, including units, zones, and sections of such a plant, the skilled person will understand how to conduct a urea production process therewith. I.e., also if not explicitly stated, the skilled person will understand the mutual arrangement of such parts. For instance, the skilled person will understand the following: A urea production plant generally comprises fluid connections and lines for process streams (urea production streams), generally including a recirculation circuit. This serves to synthesize and obtain urea, and to make optimal use of reactants by recirculation of unreacted ammonia and carbon dioxide. A urea plant generally also comprises utility connections and lines, generally including a steam circuit. This serves to provide heat where needed in the plant, and to make optimal use of available energy by circulating steam obtained in one part of the plant to another part where heat exchange from such steam can be benefited from. Thereby, also if not explicitly indicated, the person skilled in urea production will normally be able to tell which are liquid streams and which are gas streams, and through which ducts, pipes, or flow lines these are transported and/or recirculated in the plant.

Where, in this description, it is spoken of "fluid communication", this refers to any connection between a first part or section of a plant and a second part or section of a plant via which fluids, i.e., gases, liquids, or supercritical fluids, and more particularly liquids, can flow from the first part of the plant to the second part of the plant. Such fluid communication is typically provided by piping systems, hoses, or other devices well-known to the skilled person for the transportation of fluids.

Where in this description it is spoken of "gas flow connection" this refers to any connection between a first part or section of a plant and a second part or section of a plant via which gas or vapors, notably aqueous vapors, can flow from the first part of the plant to the second part of the plant. Such gas flow lines typically comprise piping systems, or other devices well-known to the skilled person for the transportation of gases, if needed under above or below (vacuum) atmospheric pressures.

The invention claimed is:

1. A process for producing urea, the process comprising
    a. subjecting ammonia and carbon dioxide to urea forming conditions in a urea synthesis section, thereby producing a urea aqueous stream;
    b. sending the urea aqueous stream to a recovery section;
    c. subjecting, in the recovery section, the urea aqueous stream to recovery of unreacted ammonia and carbon dioxide from said urea aqueous stream, thereby producing recovered ammonia and carbon dioxide, and a purified urea aqueous stream;
    d. recycling said recovered ammonia and carbon dioxide to the synthesis section;
    e. sending the purified urea aqueous stream to a concentration section;
    f. subjecting, in the concentration section, the purified urea aqueous stream to removal of water, thereby producing a concentrated urea stream; wherein the process further comprises
    g. adding, downstream of the concentration section, liquid ammonia to the concentrated urea stream, to give a concentration of ammonia after addition in the range of from 500 to 5000 ppm by weight,
    wherein the process is conducted in a urea plant provided with an abatement section for ammonia-containing gas emissions; and
    wherein the temperature of the concentrated urea stream after the addition of the liquid ammonia is 130° to 140° C., and wherein the concentrated urea stream is a urea melt with a urea concentration greater than 90 wt % and the liquid ammonia is added to the urea melt.

2. The process of claim 1, wherein the process employs a finishing section and the liquid ammonia is added downstream of the concentration section and upstream of said finishing section.

3. The process of claim 1, wherein the process employs a finishing section and the liquid ammonia is added into said finishing section.

* * * * *